(12) United States Patent
Yoshioka et al.

(10) Patent No.: US 7,906,859 B2
(45) Date of Patent: Mar. 15, 2011

(54) SEMICONDUCTOR DEVICE

(75) Inventors: Tetsuo Yoshioka, Okazaki (JP); Kenji Fukumura, Kariya (JP); Takahiko Yoshida, Okazaki (JP)

(73) Assignee: DENSO CORPORATION, Kariya (JP)

( * ) Notice: Subject to any disclaimer, the term of this patent is extended or adjusted under 35 U.S.C. 154(b) by 140 days.

(21) Appl. No.: 12/222,558

(22) Filed: Aug. 12, 2008

(65) Prior Publication Data

US 2009/0051052 A1    Feb. 26, 2009

(30) Foreign Application Priority Data

Aug. 22, 2007   (JP) ................. 2007-215977

(51) Int. Cl.
*H01L 21/31* (2006.01)
(52) U.S. Cl. ................. 257/788; 257/E23.117
(58) Field of Classification Search ........... 257/787, 257/788, E23.117, 433, 779–786, 789–790
See application file for complete search history.

(56) References Cited

U.S. PATENT DOCUMENTS

| 6,060,774 | A | 5/2000 | Terui | |
| 7,230,309 | B2 * | 6/2007 | Bauer et al. | 257/433 |
| 2009/0046183 | A1 | 2/2009 | Nishida et al. | |
| 2009/0053850 | A1 | 2/2009 | Nishida et al. | |

FOREIGN PATENT DOCUMENTS

| JP | A-04-142751 | 5/1992 |
| JP | A-05-136298 | 6/1993 |
| JP | A-05-183072 | 7/1993 |
| JP | A-06-085132 | 3/1994 |
| JP | A-08-031989 | 2/1996 |
| JP | A-09-289269 | 11/1997 |
| JP | A-2005-203431 | 7/2005 |

OTHER PUBLICATIONS

Office Action mailed Jul. 21, 2009 from Japan Patent Office in the corresponding Japanese Patent Application No. 2007-215977 (and English translation).

* cited by examiner

*Primary Examiner* — Davienne Monbleau
*Assistant Examiner* — Hoa B Trinh
(74) *Attorney, Agent, or Firm* — Posz Law Group, PLC

(57) ABSTRACT

A semiconductor device includes a molding resin layer and a semiconductor element encapsulated with the molding resin layer. The molding resin layer has an opening. A surface of the semiconductor element is partially exposed outside the molding resin layer through the opening. A groove is located in the surface of the semiconductor element around the opening of the molding resin layer. The groove is filled with the molding resin layer to produce anchor effect that enhances adhesive force of the molding resin layer to the surface of the semiconductor element around the opening.

10 Claims, 8 Drawing Sheets

FIG. 5A
FIG. 5B
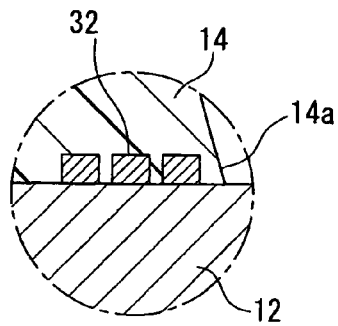
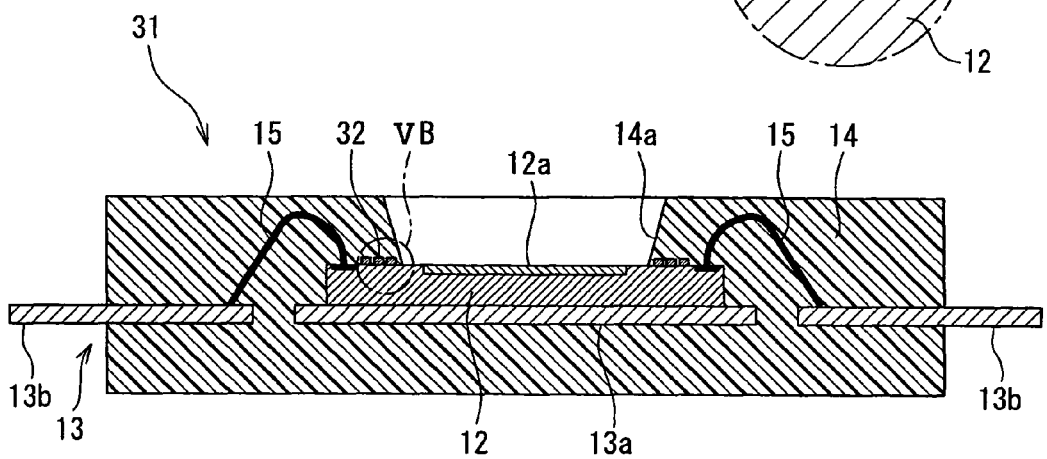
FIG. 6A
FIG. 6B
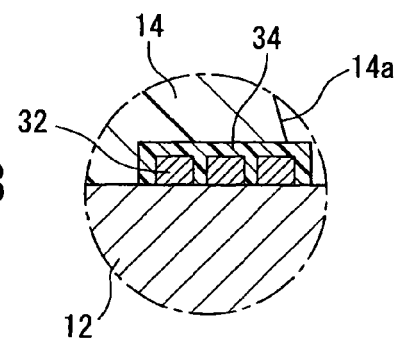
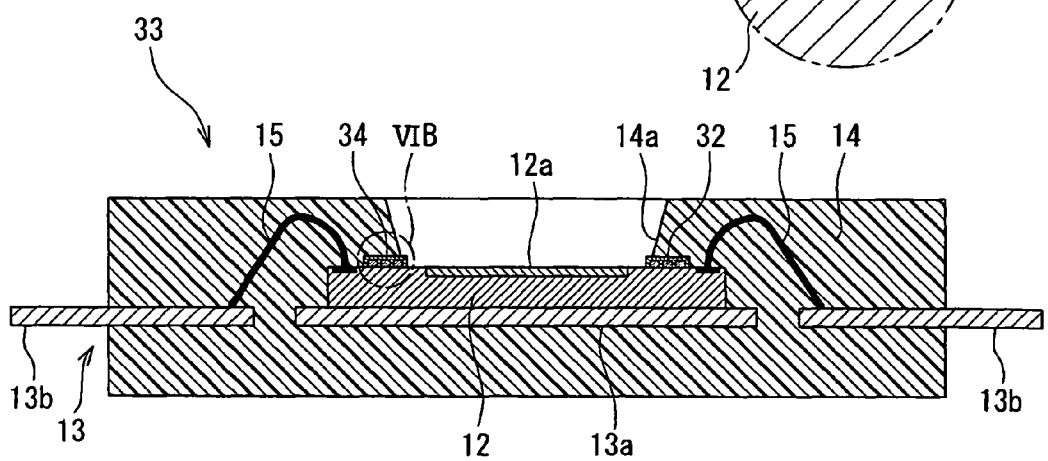

FIG. 7
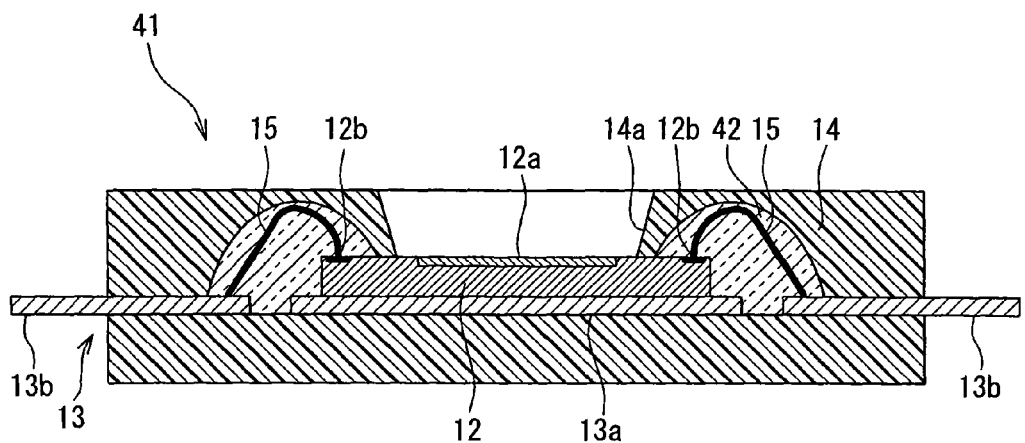
FIG. 8A  FIG. 8B
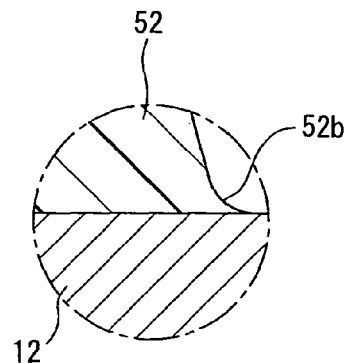
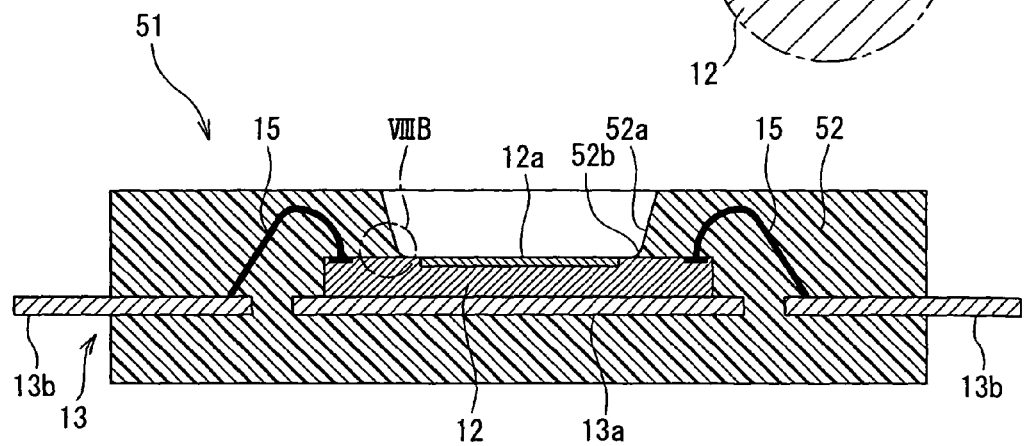

FIG. 9A
FIG. 9B
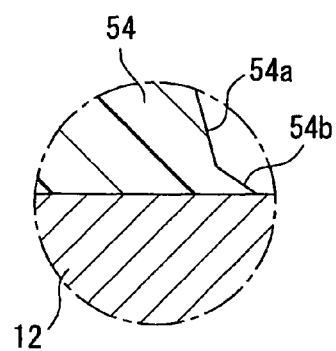
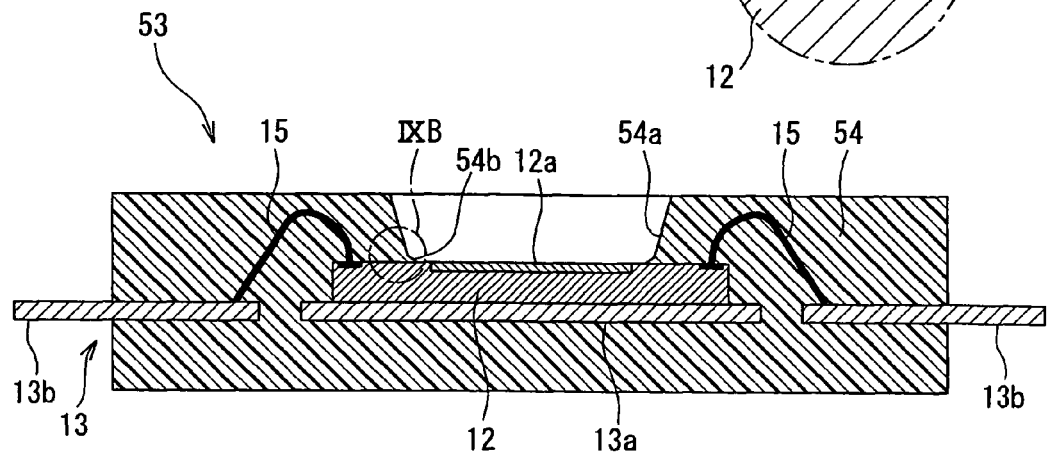
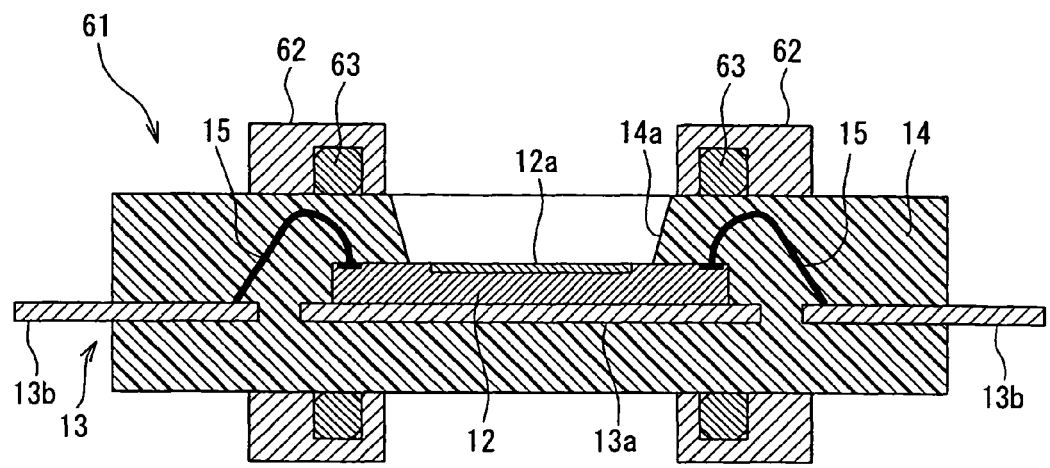
FIG. 10

<u>PRIOR ART</u>

SEMICONDUCTOR DEVICE

CROSS REFERENCE TO RELATED APPLICATION

This application is based on and incorporates herein by reference Japanese Patent Application No. 2007-215977 filed on Aug. 22, 2007.

FIELD OF THE INVENTION

The present invention relates to a semiconductor device including a semiconductor element encapsulated with a molding resin layer having an opening through which the semiconductor element is partially exposed outside the molding resin layer.

BACKGROUND OF THE INVENTION

FIG. 16 illustrates a semiconductor sensor 1 disclosed in JP-A-2005-203431. The semiconductor sensor 1 is used to detect alcohol concentration. The semiconductor sensor 1 includes a semiconductor element 2 bonded on a die pad 3 of a lead frame. Bonding pads (not shown) located around the perimeter of a front surface of the semiconductor element 2 are electrically connected via bonding wires to lead fingers of the lead frame. The semiconductor element 2 is encapsulated with a molding resin layer 4 having an opening 4a. An alcohol concentration detection portion 2a is located in the center of the front surface of the semiconductor element 2 and exposed outside the molding resin layer 4 through the opening 4a.

The semiconductor element 2 is encapsulated with the molding resin layer 4 by the following method. The semiconductor element 2 bonded on the lead frame is placed in a mold, and then liquid (or gelled) resin is injected into the mold and hardened. An upper part of the mold is provided with a projection portion that is positioned in the center of the front surface of the semiconductor element 2. Thus, the projection portion causes the molding resin layer 4 to have the opening 4a. Alternatively, as disclosed in Japanese Patent No. 2598161, the opening 4a can be formed by arranging tube-shaped objects between the upper part of the mold and the front surface of the semiconductor element 2 so that the resin can be prevented by the tube-shaped objects from entering space between the upper part of the mold and the front surface of the semiconductor element 2.

When the semiconductor sensor 1 is used in a vehicle, the semiconductor sensor 1 is subjected to severe environmental conditions, which can corrode and degrade the semiconductor sensor 1. For example, the semiconductor sensor 1 is exposed to vibration, moisture, fuel, oil, acid, alkali, and the like. Further, a temperature in the vehicle ranges from minus several tens of degrees Celsius (e.g., −40° C.) to one hundred and several tens of degrees Celsius (e.g., 150° C.). Therefore, the semiconductor sensor 1 is exposed to a repeated thermal cycle.

The repeated thermal cycle can cause the semiconductor sensor 1 to be warped due to differences in coefficients of thermal expansion between the semiconductor element 2, the die pad 3, and the molding resin layer 14. When the semiconductor sensor 1 is warped, it is likely that the molding resin layer 4 is cracked or peeled off from the front surface of the semiconductor element 2 around the opening 4a, as indicated by arrows in FIG. 16.

Further, the severe environmental conditions can advance (i.e., worsen) the crack or the peel of the molding resin layer 4. If the crack or the peel of the molding resin layer 4 is advanced to the electrode pads of the semiconductor element 2, the electrode pads are corroded, and the bonding wires are damaged. As a result, the semiconductor element 2 is electrically disconnected from the lead frame so that the semiconductor sensor 1 can be broken.

SUMMARY OF THE INVENTION

In view of the above-described problem, it is an object of the present invention to provide a semiconductor device including a semiconductor element encapsulated with a molding resin layer having an opening through which the semiconductor element is partially exposed outside the molding resin layer. The semiconductor device is constructed to prevent problems caused by a crack and a peel of the molding resin layer around the opening.

According to a first aspect of the present invention, a semiconductor device includes a molding resin layer, a semiconductor element, and a fixing member. The molding resin layer has an opening. The semiconductor element is encapsulated with the molding resin layer. A surface of the semiconductor element is exposed outside the molding resin layer through the opening. The fixing member improves fixation of the molding resin layer to the surface of the semiconductor element around the opening.

According to a second aspect of the present invention, a semiconductor device includes a molding resin layer, a semiconductor element, and a protection layer. The molding resin layer has an opening. The semiconductor element is encapsulated with the molding resin layer. The semiconductor element has a surface and an electrical terminal located on an outer periphery of the surface. The protection layer is chemically joined to the surface of the semiconductor element. A center of the surface of the semiconductor element is exposed outside the molding resin layer through the opening. The electrical terminal is encapsulated with the protection layer. The protection layer is encapsulated with the molding resin layer.

According to a second aspect of the present invention, a semiconductor device includes a molding resin layer, a semiconductor element, and a cover layer. The molding resin layer has an opening. The semiconductor element is encapsulated with the molding resin layer. A surface of the semiconductor element is partially exposed outside the molding resin layer through the opening. The cover layer covers at least a boundary between an inner edge of the opening of the molding resin layer and the exposed surface of the semiconductor element.

BRIEF DESCRIPTION OF THE DRAWINGS

The above and other objectives, features and advantages of the present invention will become more apparent from the following detailed description made with check to the accompanying drawings. In the drawings:

FIG. 5A is a diagram illustrating a cross-sectional view of a semiconductor sensor according to a fourth embodiment of the present invention, and FIG. 5B is a diagram illustrating a partially enlarged view of FIG. 5A;

FIG. 6A is a diagram illustrating a cross-sectional view of a semiconductor sensor according to a fifth embodiment of the present invention, and FIG. 6B is a diagram illustrating a partially enlarged view of FIG. 6A;

FIG. 7 is a diagram illustrating a cross-sectional view of a semiconductor sensor according to a sixth embodiment of the present invention;

FIG. 8A is a diagram illustrating a cross-sectional view of a semiconductor sensor according to a seventh embodiment of the present invention, and FIG. 8B is a diagram illustrating a partially enlarged view of FIG. 8A;

FIG. 9A is a diagram illustrating a cross-sectional view of a semiconductor sensor according to an eighth embodiment of the present invention, and FIG. 9B is a diagram illustrating a partially enlarged view of FIG. 9A;

FIG. 10 is a diagram illustrating a cross-sectional view of a semiconductor sensor according to a ninth embodiment of the present invention;

DETAILED DESCRIPTION OF THE PREFERRED EMBODIMENTS

First Embodiment

Figure 1:
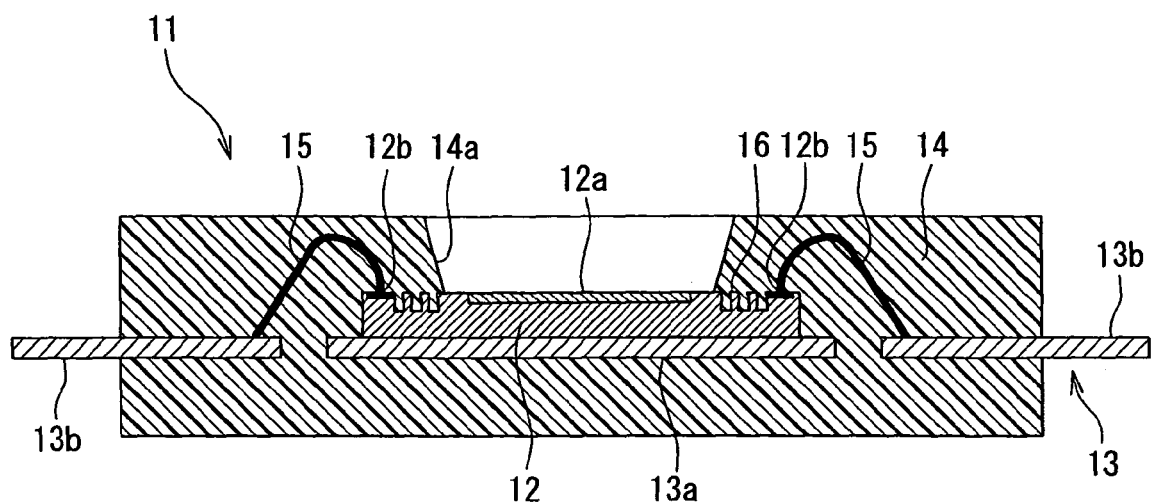
FIG. 1 is a diagram illustrating a cross-sectional view of a semiconductor sensor according to a first embodiment of the present invention.
Figure 2:
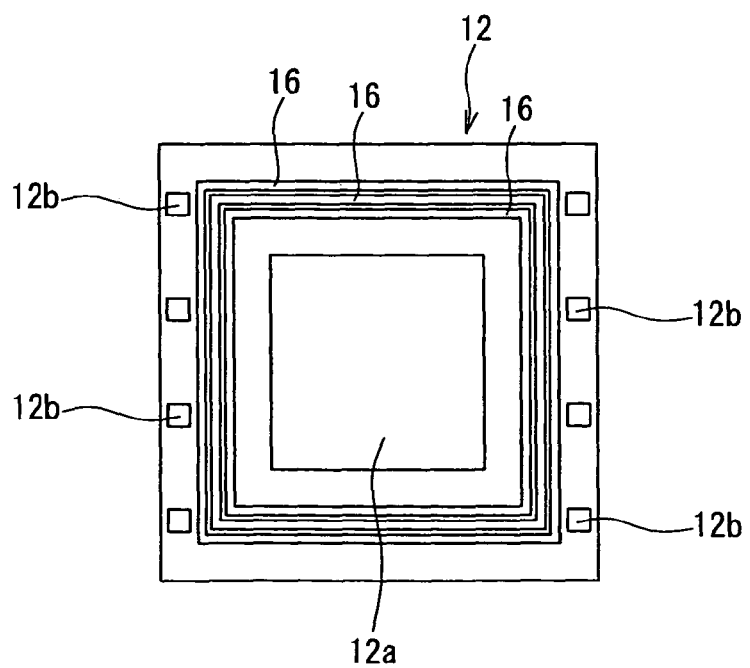
FIG. 2 is a diagram illustrating a top view of a semiconductor element of the semiconductor sensor of FIG. 1.

Referring to FIGS. 1 and 2, a semiconductor sensor 11 according to a first embodiment of the present invention includes a rectangular-shaped semiconductor element (chip) 12, a lead frame 13, and a molding resin layer 14 made of, for example, epoxy resin, polyetheretherketone (PEEK) resin, phenolic resin, or the like. For example, the semiconductor sensor 11 is mounted on a vehicle and measures physical quantity such as dielectric constant, electric conductivity, alcohol concentration in gasoline, or the like. Alternatively, the semiconductor sensor 11 can be configured as an optical device.

The semiconductor element 12 is mounted on the lead frame 13 and encapsulated with the molding resin layer 14.

The lead frame 13 includes a die pad 13a and multiple lead fingers 13b. The semiconductor element 12 is mounded on the die pad 13a. The lead fingers 13b connect the semiconductor element 12 to external circuitry.

As shown in FIG. 2, a rectangular-shaped detection portion 12a is located approximately in the center of a front surface of the semiconductor element 12. Bonding pads 12b are located on an outer periphery of the front surface of the semiconductor element 12. The semiconductor element 12 is fixed on a front surface of the die pad 13a of the lead frame 13, for example, through an adhesive. Each bonding pad 12b of the semiconductor element 12 is electrically connected to the corresponding lead finger 13b of the lead frame 13 through a bonding wire 15. The bonding wire 15 can be made of gold (Au), aluminum (Al), or the like.

The molding resin layer 14 is rectangular-shaped so that the entire periphery of the semiconductor element 12 can be encapsulated with the molding resin layer 14. The molding resin layer 14 has a tapered opening 14a through which the detection portion 12a of the semiconductor element 12 is exposed outside the molding resin layer 14. That is, the detection portion 12a is not encapsulated with the molding resin layer 14. Each lead finger 13b is exposed outside the molding resin layer 14 at one end.

As shown in FIG. 2, three grooves 16 are formed in the front surface of the semiconductor element 12 around the opening 14a of the molding resin layer 14. Each groove 16 is located between the detection portion 12a and the bonding pads 12b of the semiconductor element 12. Each groove 16 extends in a rectangular circle, and the detection portion 12a is located inside the rectangular circle. Thus, the detection portion 12a is surrounded by the grooves 16. For example, the grooves 16 can be formed by etching the front surface (a substrate itself or a protection film on the substrate) of the semiconductor element 12 in a groove pattern.

For example, the semiconductor sensor 11 can be formed as follows Firstly, the semiconductor element 12 is fixed on the die pad 13a of the lead frame 13. Then, the bonding pad 12b of the semiconductor element 12 is electrically connected to the lead finger 13b of the lead frame 13 through the bonding wire 15. Then, the semiconductor element 12 and the lead frame 13 are encapsulated with the molding resin layer 14.

The encapsulation process is performed using a mold (not shown), for example, consisting of upper and lower parts. The upper part is provided with a projection portion corresponding to the opening 14a of the molding resin layer 14. When the upper and lower parts of the mold are attached together, cavity having a shape corresponding to an outer shape of the molding resin layer 14 is formed between the upper and lower parts. In the encapsulation process, the lead frame 13, on which the semiconductor element 12 is mounted, is placed in a predetermined location in the lower part of the mold. Then, the upper part is attached to the lower part so that the projection portion of the upper part can be located on the detection portion 12a of the semiconductor element 12.

Then, a molding compound (e.g., epoxy resin, PEEK resin, and phenolic resin) is injected into the cavity of the mold and hardened. Thus, the semiconductor element 12 and the lead frame 13 are encapsulated with the molding resin layer 14 in such a manner that the detection portion 12a of the semiconductor element 12 is exposed outside the molding resin layer 14 through the opening 14a. Electrical junctions between the bonding wire 15 and each of the bonding pad 12b and the lead finger 13b are encapsulated with the molding resin layer 14. In this case, the molding compound enters the grooves 16 in the front surface of the semiconductor element 12 and is then hardened. Thus, the grooves 16 are filled with the molding resin layer 14.

When the semiconductor sensor 11 is mounted on the vehicle, the semiconductor sensor 11 is subjected to severe environmental conditions, which can corrode and degrade the semiconductor sensor 11. For example, the semiconductor sensor 11 can be exposed to vibration, moisture, fuel, oil, acid, alkali, and the like. Further, a temperature in the vehicle, where the semiconductor sensor 11 is mounted, can range from minus several tens of degrees Celsius (e.g., −40° C.) to one hundred and several tens of degrees Celsius (e.g., 150° C.). Therefore, the semiconductor sensor 11 is exposed to a repeated thermal cycle.

The repeated thermal cycle may cause the semiconductor sensor 11 to be warped due to differences in coefficients of thermal expansion between the semiconductor element 12, the die pad 13a, and the molding resin layer 14. When the semiconductor sensor 11 is warped, the molding resin layer 14 may be cracked or peeled off from the front surface of the semiconductor element 12 around the opening 14a.

Figure 16:
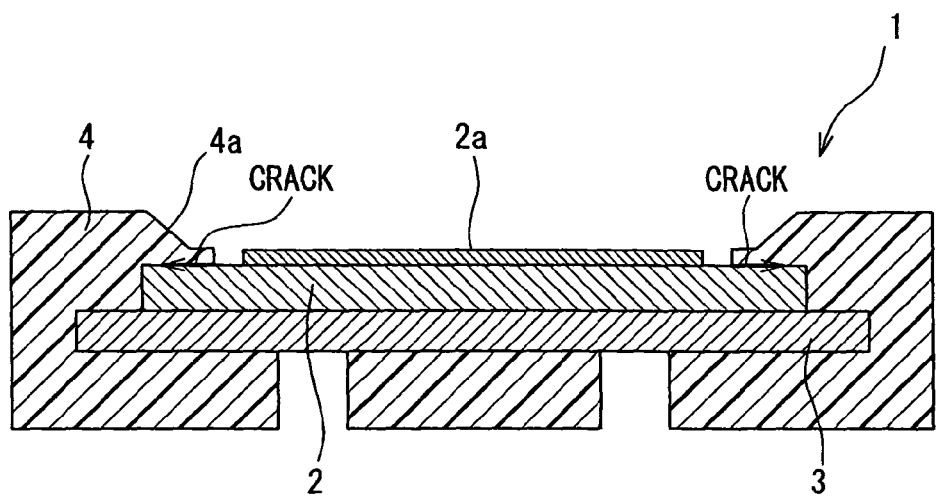
FIG. 16 is a diagram illustrating a cross-sectional view of a conventional semiconductor sensor.

The semiconductor sensor 11 according to the first embodiment is configured to avoid the crack and the peel of the molding resin layer 14. Specifically, the semiconductor sensor 11 has the groove 16, which is formed in the front surface of the semiconductor element 12 around the opening 14a of the molding resin layer 14. The groove 16 is filled with the molding resin layer 14 so that an anchor effect can be produced. The anchor effect can improve adhesive strength of the molding resin layer 14 to the front surface of the semiconductor element 12 around the opening 14a. In this way, the groove 16 can help prevent the molding resin layer 14 from being cracked or peeled off from the front surface of the semiconductor element 12. Therefore, as compared to the conventional semiconductor sensor 1 shown in FIG. 16, the semiconductor sensor 11 can have long lifetime and can be reliably used under severe environmental conditions.

Second Embodiment

Figure 3A:
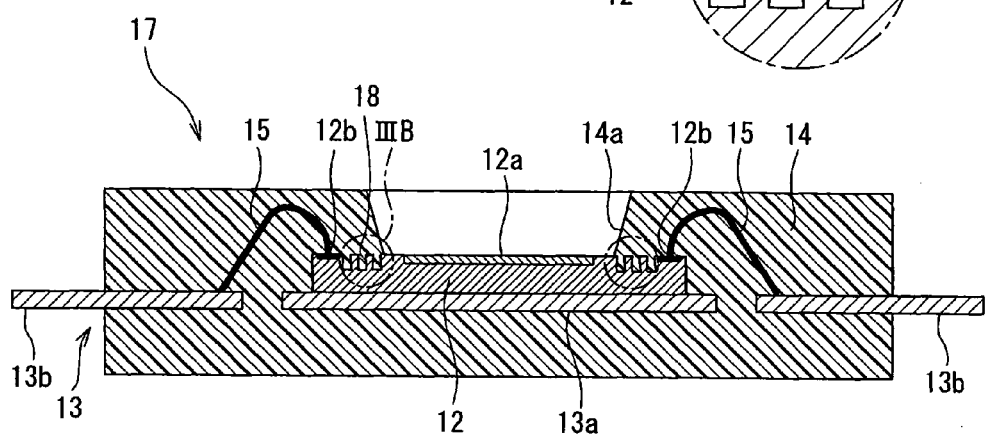
FIG. 3A is a diagram illustrating a cross-sectional view of a semiconductor sensor according to a second embodiment of the present invention.
Figure 3B:
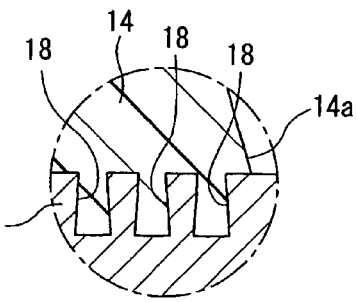
FIG. 3B is a diagram illustrating a partially enlarged view of FIG. 3A.

A semiconductor sensor 17 according to a second embodiment of the present invention is described below with reference to FIGS. 3A and 3B. A difference between the first and second embodiments is in the shape of the grooves formed in the front surface of the semiconductor element 12 around the opening 14a of the molding resin layer 14.

The semiconductor sensor 17 has three grooves 18 instead of the grooves 16. As shown in detail in FIG. 3B, each groove 18 has a reverse tapered shape in cross-section. That is, the groove 18 gradually narrows from its opening toward its bottom. The reverse tapered shape enhances the anchor effect so that the adhesive strength of the molding resin layer 14 to the front surface of the semiconductor element 12 can be more improved. For example, the groove 18 can be formed by microfabrication techniques using reactive ion etching (RIE).

In the first and second embodiments described above, the grooves 16, 18 formed in the front surface of the semiconductor element 12 improve the adhesive strength of the molding resin layer 14 to the front surface of the semiconductor element 12 around the opening 14a. That is, the grooves 16, 18 can serve as a fixing member that improves fixation of the molding resin layer 14 to the front surface of the semiconductor element 12 around the opening 14a. An uneven portion of the front surface of the semiconductor element 12 can serve as the fixing member. The uneven portion can have a shape other than a groove. For example, the uneven portion can be formed by simply roughening the front surface of the semiconductor element 12 by etching or spattering techniques. The uneven portion can be patterned like a dot, a line, a grid, or the like. The uneven portion can be formed in the front surface of the semiconductor element 12 wholly or partially around the opening 14a of the molding resin layer 14. For example, the uneven portion can be formed in a region except for a wiring portion that connects the detection portion 12a to the bonding pad 12b.

Third Embodiment

Figure 4A:
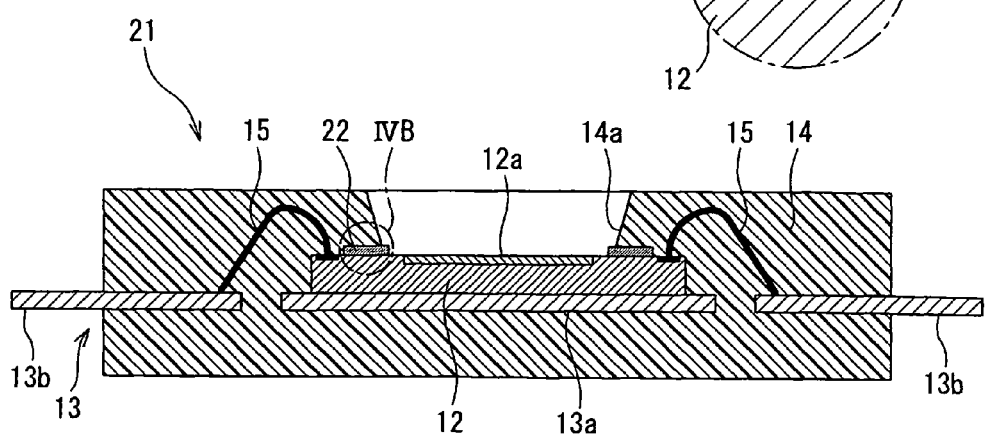
FIG. 4A is a diagram illustrating a cross-sectional view of a semiconductor sensor according to a third embodiment of the present invention.
Figure 4B:
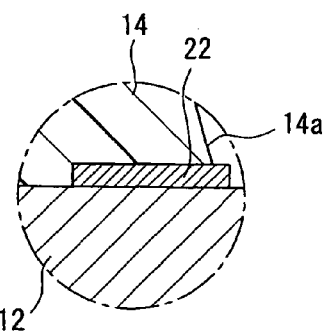
FIG. 4B is a diagram illustrating a partially enlarged view of FIG. 4A.

A semiconductor sensor 21 according to a third embodiment of the present invention is described below with reference to FIGS. 4A and 4B. A difference between the first and third embodiments is as follows. The semiconductor sensor 21 has an adhesive member 22 instead of the grooves 16. The adhesive member 22 is located on the front surface of the semiconductor element 12 around the opening 14a of the molding resin layer 14. Thus, the molding resin layer 14 can be tightly fixed to the front surface of the semiconductor element 12 around the opening 14a. The adhesive member 22 has a coefficient of thermal expansion that is intermediate between coefficients of thermal expansion of the semiconductor element 12 and the molding resin layer 14. For example, the adhesive member 22 can be a filler-added epoxy adhesive agent, a ceramic adhesive agent, or the like.

Before the encapsulation process is performed, the adhesive member 22 in the form of liquid is applied to the front surface of the semiconductor element 12 between the detection portion 12a and the bonding pad 12b. The adhesive member 22 is bonded to each of the semiconductor element 12 and the molding resin layer 14 by heat produced during the encapsulation process. As a result, the semiconductor element 12 and the molding resin layer 14 are tightly bonded together through the adhesive member 22. Alternatively, before the encapsulation process is performed, the adhesive member 22 in the form of film can be disposed on the front surface of the semiconductor element 12 between the detection portion 12a and the bonding pad 12b. The film adhesive member 22 is melted by the heat produced during the encapsulation process so that the semiconductor element 12 and the molding resin layer 14 can be tightly bonded together through the adhesive member 22.

As described above, according to the third embodiment, the adhesive member 22 is located between the front surface of the semiconductor element 12 and the molding resin layer 14 around the opening 14a. The adhesive member 22 improves the adhesive strength of the molding resin layer 14 to the front surface of the semiconductor element 12 around the opening 14a. Therefore, the adhesive member 22 can serve as the fixing member that improves the fixation of the molding resin layer 14 to the front surface of the semiconductor element 12 around the opening 14a.

Further, the adhesive member 22 has a coefficient of thermal expansion that is intermediate between coefficients of thermal expansion of the semiconductor element 12 and the molding resin layer 14. Therefore, the adhesive member 22 can help reduce stress caused by a difference in the coefficients of thermal expansion between the semiconductor element 12 and the molding resin layer 14. Thus, the adhesive member 22 can effectively help prevent the molding resin layer 14 from being cracked or peeled off from the front surface of the semiconductor element 12.

The third embodiment can be modified in various ways. For example, the adhesive member 22 can have a Young's modulus smaller than that of the molding resin layer 14. Specifically, the adhesive member 22 can have a Young's modulus equal to or less than 1 MPa. Since such a small Young's modulus causes the adhesive member 22 to be relatively soft, the adhesive member 22 can serve not only as an adhesive but also as a cushion. In such an approach, the adhesive member 22 can absorb differences in thermal expansion and contraction between the semiconductor element 12 and the molding resin layer 14. Thus, the adhesive member 22 can effectively help prevent the molding resin layer 14 from being cracked or peeled off from the front surface of the semiconductor element 12.

Fourth Embodiment

A semiconductor sensor 31 according to a fourth embodiment of the present invention is described below with reference to FIGS. 5A and 5B. A difference between the first and fourth embodiments is as follows. The semiconductor sensor 31 has a heating element 32 instead of the groove 16. The heating element 32 is located on the front surface of the semiconductor element 12 around the opening 14a of the molding resin layer 14. The heating element 32 is wholly or partially encapsulated with the molding resin layer 14. For example, the heating element 32 is made of a metallic material (e.g., aluminum, gold, or polysilicon) and extends in a triple rectangular helical fashion to surround the detection portion 12a. The heating element 32 is electrically connected to the bonding pad 12b and can be energized by external circuitry via the bonding pad 12b. The heating element 32 can be easily formed during manufacturing process of the semiconductor sensor 31.

The heating element 32 is energized after the encapsulating process is finished. As a result, the heating element 32 heats the molding resin layer 14 around the opening 14a so that the molding resin layer 14 can be tightly joined to the front surface of the semiconductor device 12. Thus, the heating element 32 can help prevent the molding resin layer 14 from being cracked or peeled off from the front surface of the semiconductor element 12 around the opening 14a. Therefore, the heating element 32 can serve as the fixing member that improves the fixation of the molding resin layer 14 to the front surface of the semiconductor element 12 around the opening 14a.

Fifth Embodiment

A semiconductor sensor 33 according to a fifth embodiment of the present invention is described below with reference to FIGS. 6A, 6B. A difference between the fourth and fifth embodiments is as follows. The semiconductor sensor 33 has a thermal adhesive member 34 in addition to the heating element 32. A surface of the heating element 32 is wholly or partially covered with the thermal adhesive member 34. For example, the thermal adhesive member 34 can be made of thermoplastic elastomer.

The heating element 32 is energized after the encapsulation process is finished. As a result, the heating element 32 heats the thermal adhesive member 34 so that the semiconductor element 12 and the molding resin layer 14 can be tightly bonded together through the thermal adhesive member 34. Thus, the thermal adhesive member 34 can help prevent the molding resin layer 14 from being cracked or peeled off from the front surface of the semiconductor element 12 around the opening 14a. Therefore, the heating element 32 and the thermal adhesive member 34 can serve as the fixing member that improves the fixation of the molding resin layer 14 to the front surface of the semiconductor element 12 around the opening 14a. The thermal adhesive member 34 can be made of a material other than thermoplastic elastomer. For example, the thermal adhesive member 34 can be made of tetrafluoroethylene perfluoroalkoxy vinyl ether copolymer (PFA), fluorinated ethylene propylene copolymer (FEP), polyester, or the like.

Sixth Embodiment

A semiconductor sensor 41 according to a sixth embodiment of the present invention is described below with reference to FIG. 7. A difference between the first and sixth embodiments is as follows. The semiconductor sensor 41 has a protection member 42 instead of the groove 16. The bonding pad 12b, the bonding wire 15, and electrical junctions between the bonding wire 15 and each of the bonding pad 12b and the lead finger 13b are encapsulated with the protection member 42. Then, the protection member 42 is encapsulated with the molding resin layer 14. The protection member 42 is made of a material that can be chemically joined to a surface material of the semiconductor element 12. For example, the protection member 42 can be made of glass that can be chemically joined to an oxide film formed on the surface of the semiconductor element 12.

For example, the semiconductor sensor 41 can be formed as follows. Firstly, the semiconductor element 12 is fixed on the die pad 13a of the lead frame 13. Then, the bonding pad 12b of the semiconductor element 12 is electrically connected to the lead finger 13b of the lead frame 13 through the bonding wire 15. Then, the bonding pad 12b, the bonding wire 15, and the electrical junctions between the bonding wire 15 and each of the bonding pad 12b and the lead finger 13b are encapsulated with the protection member 42. Then, the semiconductor element 12, the lead frame 13, and the protection member 42 are encapsulated with the molding resin layer 14.

According to the sixth embodiment, electrical connections between the semiconductor element 12 and the lead finger 13b are encapsulated with the protection member 42 such as glass. In such an approach, even if the molding resin layer 14 is cracked or peeled off from the front surface of the semiconductor element 12 around the opening 14a, the crack or peel of the molding resin layer 14 stops at the protection member 42. Since the protection member 42 is chemically joined to the surface of the semiconductor element 12, the semiconductor element 12 and the protection member 42 are tightly joined together. Thus, the protection member 42 can be prevented from being clacked or peeled off from the semiconductor element 12. In summary, even if the molding resin layer 14 is cracked or peeled off from the front surface of the semiconductor element 12, the electrical connections between the semiconductor element 12 and the lead finger 13b can be protected by the protection member 42. Therefore, as compared to the conventional semiconductor sensor 1 shown in FIG. 16, the semiconductor sensor 41 can have long lifetime and can be reliably used under severe environmental conditions.

Seventh Embodiment

A semiconductor sensor 51 according to a seventh embodiment of the present invention is described below with reference to FIGS. 8A and 8B. A difference between the first and seventh embodiments is as follows. The semiconductor sensor 51 has an edge portion 52b instead of the groove 16. The edge portion 52b is integrally formed with a molding resin layer 52 to provide an inner edge of an opening 52a of the molding resin layer 52. That is, the molding resin layer 52 and the edge portion 52b are formed as one piece.

As shown in detail in FIG. 8B, the edge portion 52b of the molding resin layer 52 has a bottom surface and a rounded side surface. The bottom surface of the edge portion 52b is located on (i.e., in contact with) the front surface of the semiconductor element 12. The rounded side surface of the edge portion 52b forms a substantially acute angle with the front surface of the semiconductor element 12.

According to the seventh embodiment, the edge portion 52b of the molding resin layer 52 forms a substantially acute angle with the front surface of the semiconductor element 12.

In such a approach, stress exerted between the front surface of the semiconductor element 12 and the molding resin layer 52 around the opening 52a can be reduced, as compared to when the edge portion 52b forms a right angle with the front surface of the semiconductor element 12. Thus, the edge portion 52b can help prevent the molding resin layer 52 from being cracked or peeled off from the front surface of the semiconductor element 12 around the opening 52a. Therefore, the edge portion 52b can serve as the fixing member that improves the fixation of the molding resin layer 52 to the front surface of the semiconductor element 12 around the opening 52a. Further, since the molding resin layer 52 and the edge portion 52b are formed as one piece, the edge portion 52b can be easily formed at low cost.

Eighth Embodiment

A semiconductor sensor 53 according to an eighth embodiment of the present invention is described below with reference to FIGS. 9A and 9B. A difference between the seventh and eighth embodiments is as follows. The semiconductor sensor 53 has an edge portion 54b instead of the edge portion 52b. The edge portion 54b is integrally formed with a molding resin layer 54 to provide an inner edge of an opening 54a of the molding resin layer 54. That is, the molding resin layer 54 and the edge portion 54b are formed as one piece.

As shown in detail in FIG. 9B, the edge portion 54b of the molding resin layer 54 has a bottom surface and a flat side surface. The bottom surface of the edge portion 54b is located on (i.e., in contact with) the front surface of the semiconductor element 12. The flat side surface of the edge portion 54b forms an acute angle with the front surface of the semiconductor element 12.

According to the eighth embodiment, the edge portion 54b of the molding resin layer 54 forms an acute angle with the front surface of the semiconductor element 12. Therefore, the semiconductor sensor 53 of the eighth embodiment can have the same effect as the semiconductor sensor 51 of the seventh embodiment.

Ninth Embodiment

A semiconductor sensor 61 according to a ninth embodiment of the present invention is described below with reference to FIG. 10. A difference between the first and ninth embodiments is as follows. The semiconductor sensor 61 has a cramp 62 that tightly fastens the molding resin layer 14 to the semiconductor element 12 around the opening 14a. For example, the cramp 62 is a C-shaped metal spring and placed through an O-ring 63 on each opposite side across the opening 14a.

According to the ninth embodiment, the semiconductor element 12 and the molding resin layer 14 are mechanically fastened together by the cramp 62. Thus, the clamp 62 can help prevent the molding resin layer 14 from being cracked or peeled off from the front surface of the semiconductor element 12 around the opening 14a. Therefore, the cramp 62 can serve as the fixing member that improves the fixation of the molding resin layer 14 to the front surface of the semiconductor element 12 around the opening 14a.

The cramp 62 can have a shape and a structure other than the C-shaped metal spring. For example, the cramp 62 can be constructed with two separate pieces that are respectively placed on top and bottom surfaces of the molding resin layer 14 and fastened together by a screw.

Tenth Embodiment

Figure 11:
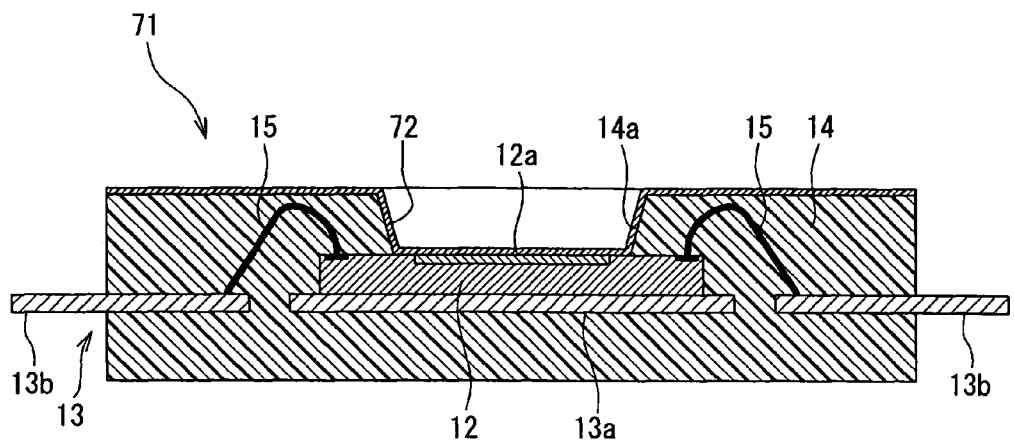
FIG. 11 is a diagram illustrating a cross-sectional view of a semiconductor sensor according to a tenth embodiment of the present invention.

A semiconductor sensor 71 according to a tenth embodiment of the present invention is described below with reference to FIG. 11. A difference between the first and tenth embodiments is as follows. The semiconductor sensor 71 has a cover member 72 that cover at least a boundary between an inner edge of the opening 14a of the molding resin layer 14 and the exposed front surface of the semiconductor element 12. In the tenth embodiment, as shown in FIG. 11, the surface of the molding resin layer 14 and the exposed front surface of the semiconductor element 12 are wholly covered with the cover member 72. As a result, the detection portion 12a located on the front surface of the semiconductor element 12 is covered with the cover member 72.

The cover member 72 can be made of a fluorinated coating material, which has a water repellency, an oil repellency, a moisture-proof property, an insulation property, a chemical resistance, an osmotic resistance, an antifouling property, and/or the like. For example, the cover member 72 can be made of teflon (trademark of Dupont). For example, the cover member 72 can be formed by sputtering a solid coating material onto the boundary. Alternatively, the cover member 72 can be formed by spraying or applying a liquid coating material onto the boundary and then by hardening the liquid coating material.

According to the tenth embodiment, the boundary between the molding resin layer 14 and the semiconductor element 12 is covered by the cover member 72. In such an approach, even if the molding resin layer 14 is cracked or peeled off from the front surface of the semiconductor element 12, the cover member 72 can prevent a foreign matter, which causes corrosion or degradation, from entering the cracked or peeled portion of the molding resin layer 14. Therefore, the cracked portion or the peeled portion of the molding resin layer 14 can be prevented from being advanced (i.e., worsened).

The detection portion 12a can be protected by the cover member 72 by covering the exposed front surface of the semiconductor element 12 with the cover member 72. When the detection portion 12a is covered with the cover member 72, a material for making the cover member 72 can be selected according to which physical quantity is detected by the semiconductor sensor 71 (i.e., the detection portion 12a). For example, the cover member 72 can be made of a material having a high translucency, a high resistivity, a dielectric constant, or the like.

Eleventh Embodiment

Figure 12:
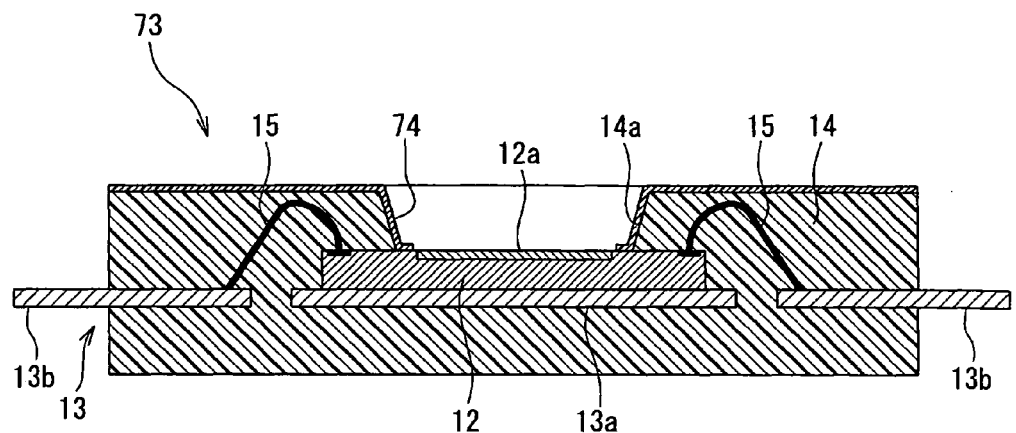
FIG. 12 is a diagram illustrating a cross-sectional view of a semiconductor sensor according to an eleventh embodiment of the present invention.

A semiconductor sensor 73 according to an eleventh embodiment of the present invention is described below with reference to FIG. 12. A difference between the tenth and eleventh embodiments is as follows.

The semiconductor sensor 73 has a cover member 74 instead of the cover member 72. Like the cover member 72, the cover member 74 covers at least the boundary between the inner edge of the opening 14a of the molding resin layer 14 and the exposed front surface of the semiconductor element 12. Unlike the cover member 72, the cover member 74 does not cover the detection portion 12a located on the front surface of the semiconductor element 12.

According to the eleventh embodiment, the boundary is covered by the cover member 74. In such an approach, even if the molding resin layer 14 is cracked or peeled off from the front surface of the semiconductor element 12, the cover member 74 can prevent the foreign matter from entering the cracked or peeled portion of the molding resin layer 14.

Twelfth Embodiment

Figure 13:
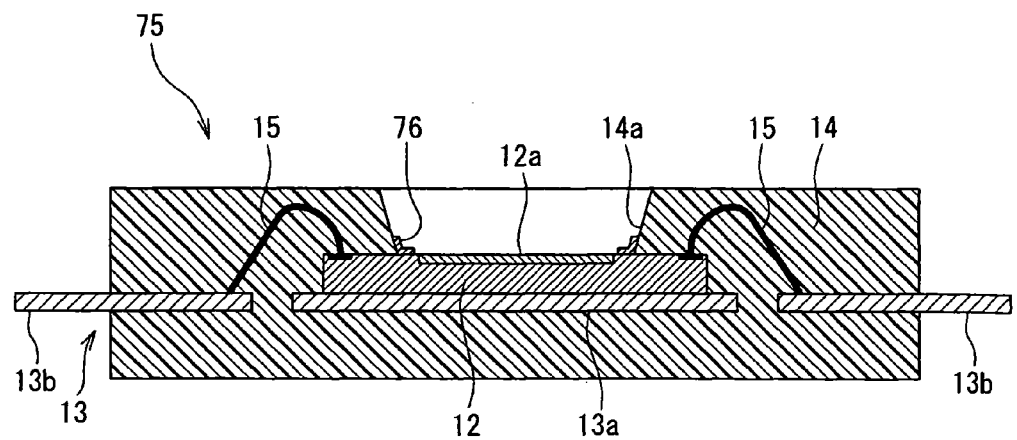
FIG. 13 is a diagram illustrating a cross-sectional view of a semiconductor sensor according to a twelfth embodiment of the present invention.

A semiconductor sensor 75 according to a twelfth embodiment of the present invention is described below with reference to FIG. 13. A difference between the tenth and twelfth embodiments is as follows.

The semiconductor sensor 75 has a cover member 76 instead of the cover member 72. Whereas the cover member 74 covers at least the boundary between the inner edge of the opening 14a of the molding resin layer 14 and the exposed front surface of the semiconductor element 12, the cover member 76 covers only the boundary.

According to the twelfth embodiment, the boundary is covered by the cover member 76. In such an approach, even if the molding resin layer 14 is cracked or peeled off from the front surface of the semiconductor element 12, the cover member 76 can prevent the foreign matter from entering the cracked or peeled portion of the molding resin layer 14.

Thirteenth Embodiment

Figure 14A:
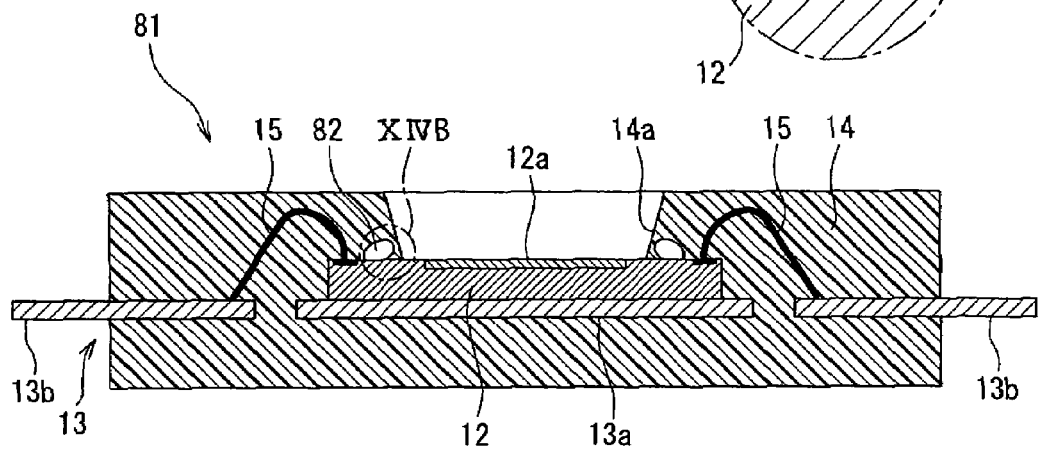
FIG. 14A is a diagram illustrating a cross-sectional view of a semiconductor sensor according to a thirteenth embodiment of the present invention.
Figure 14B:
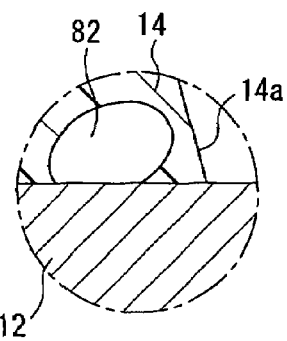
FIG. 14B is a diagram illustrating a partially enlarged view of FIG. 14A.

A semiconductor sensor 81 according to a thirteenth embodiment of the present invention is described below with reference to FIGS. 14A and 14B. A difference between the first and thirteenth embodiments is as follows. The semiconductor sensor 81 has cavity 82 instead of the groove 16. The cavity 82 is located in the molding resin layer 14 around the opening 14a to surround the detection portion 12a. The cavity 82 is in contact with the front surface of the semiconductor element 12. In the thirteenth embodiment, as shown in detail in FIG. 14B, the cavity 82 is shaped in the form of bubble in cross-section. Therefore, the cavity 82 is in contact with the front surface of the semiconductor element 12 at an acute angle.

According to the thirteenth embodiment, the cavity 82 is located in the molding resin layer 14 around the opening 14a. In such an approach, stiffness of the molding resin layer 14 is partially reduced so that stress caused by differences in thermal expansion and contraction between the semiconductor element 12 and the molding resin layer 14 can be reduced. Thus, the cavity 82 can help prevent the molding resin layer 14 from being cracked or peeled off from the front surface of the semiconductor element 12 around the opening 14a. Therefore, the cavity 82 can serve as the fixing member that improves the fixation of the molding resin layer 14 to the front surface of the semiconductor element 12 around the opening 14a. Further, even when the molding resin layer 14 is cracked or peeled off from the front surface of the semiconductor element 12, the crack or peel of the molding resin layer 14 stops at the cavity 82. Therefore, the cavity 82 can help prevent the cracked or peel of the molding resin layer 14 from being advanced (i.e., worsened).

Fourteenth Embodiment

Figure 15A:
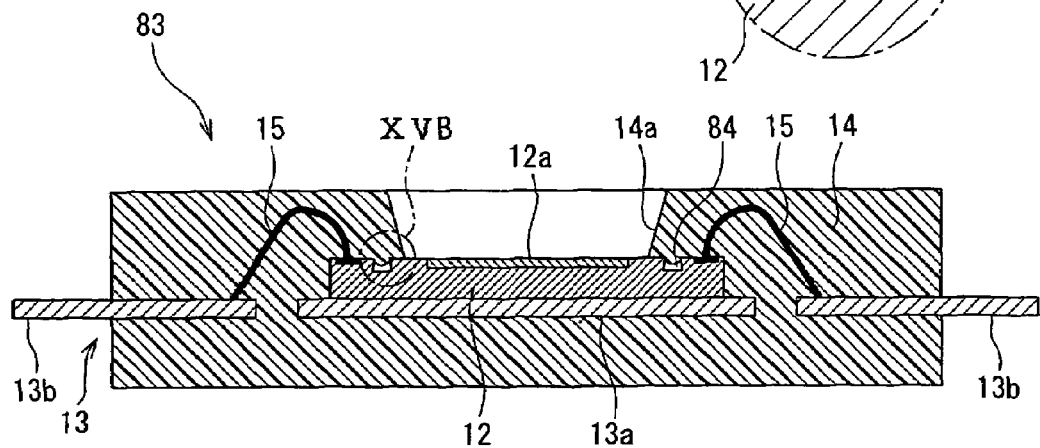
FIG. 15A is a diagram illustrating a cross-sectional view of a semiconductor sensor according to a fourteenth embodiment of the present invention.
Figure 15B:
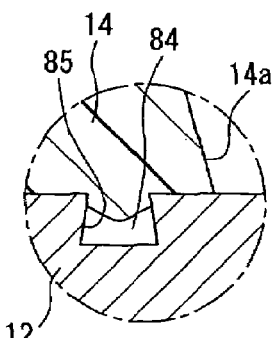
FIG. 15B is a diagram illustrating a partially enlarged view of FIG. 15A.

A semiconductor sensor 83 according to a fourteenth embodiment of the present invention is described below with reference to FIGS. 15A and 15B. A difference between the thirteenth and fourteenth embodiments is as follows. The semiconductor sensor 83 has cavity 84 instead of the cavity 82. Whereas the cavity 82 of the thirteenth embodiment is located in the molding resin layer 14, the cavity 84 of the fourteenth embodiment is located in the semiconductor element 12. Specifically, the cavity 84 is located in the front surface of the semiconductor element 12 around the opening 14a of the molding resin layer 14 and in contact with the molding resin layer 14.

For example, the cavity 84 can be formed as follows. Firstly, a recess 85 like a groove is formed in the top surface of the semiconductor element 12 around the detection portion 12a. Then, the semiconductor element 12 is encapsulated with the molding resin layer 14 in such a manner that the recess 85 is not filled with the molding resin layer 14.

According to the fourteenth embodiment, the cavity 84 is located in the semiconductor element 12 around the opening 14a. Therefore, stress caused by differences in thermal expansion and contraction between the semiconductor element 12 and the molding resin layer 14 can be reduced. Thus, the cavity 84 can help prevent the molding resin layer 14 from being cracked or peeled off from the front surface of the semiconductor element 12 around the opening 14a. Therefore, the cavity 84 can serve as the fixing member that improves the fixation of the molding resin layer 14 to the front surface of the semiconductor element 12 around the opening 14a. Further, even when the molding resin layer 14 is cracked or peeled off from the front surface of the semiconductor element 12, the crack or peel of the molding resin layer 14 stops at the cavity 84. Therefore, the cavity 84 can help prevent the cracked or peel of the molding resin layer 14 from being advanced. (i.e., worsened). Furthermore, as compared to the cavity 82, the cavity 84 can be formed easily. Also, the anchor effect can be produced by partially filling the recess 85 with the molding resin layer 14.

Modifications

The embodiments described above may be modified in various ways. For example, the shapes of the cavities 82, 84 can vary. For example, a bubble as the cavity 82 can be located (i.e., trapped) inside the molding resin layer 14 near the front surface of the semiconductor element 12. A plurality of bubbles can be formed inside the molding resin layer 14 near the front surface of the semiconductor element 12.

The embodiments can be combined with each other to produce a synergistic effect. For example, each of the first and second embodiments can be combined with each of the tenth to eleventh embodiments. In such an approach, the molding resin layer 14 is tightly fixed to the semiconductor element 12 by the grooves 16, 18, and the boundary between the molding resin layer 14 and the semiconductor element 12 is covered by the cover members 72, 74, 76. For another example, each of the thirteenth and fourteenth embodiments can be combined with the fourth embodiment. In this case, the heating element 32 of the fourth embodiment is placed at least partially inside the cavities 82, 84. In such an approach, even when the foreign matter (e.g., water, oil, or the like) causing corrosion or degradation enters the cavities 82, 84, the heating element 32 can heat the foreign matter so that the foreign matter can be volatilized or decomposed.

The semiconductor element 12 can be mounted on a base other than the lead frame 13. For example, the semiconductor element 12 can be mounted on a synthetic resin substrate, a ceramic substrate, a heat sink, or the like. In summary, the present invention can be applied to a semiconductor device including a semiconductor element encapsulated with a molding resin layer having an opening through which the semiconductor element is partially exposed outside the molding resin layer.

Such changes and modifications are to be understood as being within the scope of the present invention as defined by the appended claims.

What is claimed is:

1. A semiconductor device comprising:
   a molding resin layer having an opening; and
   a semiconductor element encapsulated with the molding resin layer, the semiconductor element having a surface partially exposed outside the molding resin layer through the opening, wherein
   the semiconductor element has an electrode pad on the surface and a groove on the surface, and wherein the groove is filled with the molding resin layer and located between the electrode pad and an exposed portion of the surface.

2. The semiconductor device according to claim 1, wherein the semiconductor device is used in a vehicle.

3. The semiconductor device according to claim 2, wherein the semiconductor device is used in fuel or oil for the vehicle.

4. The semiconductor device according to claim 2, wherein the semiconductor element further includes a detection portion located on the exposed surface, and wherein the detection portion is configured to detect concentration of alcohol in gasoline for the vehicle.

5. The semiconductor device according to claim 1, further comprising:

a bonding wire connected to the electrode pad and encapsulated with the molding resin layer.

6. The semiconductor device according to claim 5, further comprising:

a lead frame including a die pad and a lead finger, wherein the semiconductor element is mounted on the die pad, and wherein the lead finder has a first end connected to the bonding wire and a second end exposed outside the molding resin layer.

7. The semiconductor device according to claim 1, wherein the groove surrounds the exposed portion of the surface.

8. The semiconductor device according to claim 7, wherein the groove forms a rectangular circle to surround the exposed portion of the surface.

9. The semiconductor device according to claim 7, wherein the groove comprises a plurality of grooves, each groove surrounding the exposed portion of the surface.

10. The semiconductor device according to claim 1, wherein the groove has a reverse tapered section.

* * * * *